United States Patent
Pennington et al.

(10) Patent No.: US 9,891,181 B2
(45) Date of Patent: Feb. 13, 2018

(54) MEASUREMENT DEVICE FOR MEASURING A PROPERTY OF A FLOWING FLUID

(71) Applicant: Endress + Hauser Flowtec AG, Reinach (CH)

(72) Inventors: Jason Pennington, Indianapolis, IN (US); Robert Head, Indianapolis, IN (US)

(73) Assignee: Endress + Hauser Flowtec AG, Rienach (CH)

( * ) Notice: Subject to any disclaimer, the term of this patent is extended or adjusted under 35 U.S.C. 154(b) by 0 days.

(21) Appl. No.: 14/975,947

(22) Filed: Dec. 21, 2015

(65) Prior Publication Data
US 2017/0176363 A1    Jun. 22, 2017

(51) Int. Cl.
*G01N 25/18*    (2006.01)
*G01F 1/68*    (2006.01)
(Continued)

(52) U.S. Cl.
CPC ............... *G01N 25/72* (2013.01); *G01F 1/58* (2013.01); *G01F 25/0007* (2013.01)

(58) Field of Classification Search
USPC ....................... 374/5, 7; 73/204.26
See application file for complete search history.

(56) References Cited

U.S. PATENT DOCUMENTS 5,909,171 A * 6/1999 Kyrtsos ............... F16D 66/00
116/208
6,360,850 B1 * 3/2002 Odisho ............... F16D 66/024
188/1.11 L
(Continued)

FOREIGN PATENT DOCUMENTS

WO        2009134268 A1    11/2009

*Primary Examiner* — Lisa Caputo
*Assistant Examiner* — Nasir U Ahmed
(74) *Attorney, Agent, or Firm* — Bacon & Thomas, PLLC

(57) ABSTRACT

A measurement device, in particular an electromagnetic flow meter, for measuring a flow, of a flowing fluid, comprising a measurement tube having an outer tube and a liner lining an inside of the outer tube, and a measurement structure for measuring a property of a fluid flowing through the lined measurement tube during measurement operation, capable of detecting abrasion of the liner. The liner consists of a thermally insulating material, in particular a rubber or a plastic material, structure are foreseen for measuring a temperature gradient ($\Delta T$) across a measurement tube wall of the measurement tube, when the measurement tube wall is exposed to a temperature difference ($\Delta T_{L/A}$) between an ambient temperature ($T_A$) and a fluid temperature ($T_{L/A}$) of the fluid, and a detecting structure for detecting abrasion of the liner are foreseen, detecting abrasion in case a deviation between the measured temperature gradient ($\Delta T$) and a predetermined reference temperature gradient ($\Delta T_{ref}$ ($\Delta T_{L/A}$)) representing a temperature gradient across a measurement tube wall exposed to the same or at least a similar temperature difference ($\Delta T_{L/A}$) of an identical measurement tube comprising an unimpaired liner exceeds a predetermined limit.

15 Claims, 1 Drawing Sheet

(51) Int. Cl.
  *G01N 25/72* (2006.01)
  *G01F 1/58* (2006.01)
  *G01F 25/00* (2006.01)

(56) References Cited

U.S. PATENT DOCUMENTS

| | | | |
|---|---|---|---|
| 6,824,305 B1* | 11/2004 | Boyd | G01K 17/00 |
| | | | 374/15 |
| 2005/0183514 A1 | 8/2005 | Huybrechts | |
| 2005/0193833 A1* | 9/2005 | Huybrechts | G01F 1/588 |
| | | | 73/861.12 |
| 2008/0163692 A1 | 7/2008 | Huang | |
| 2010/0206090 A1 | 8/2010 | Stack | |
| 2013/0031973 A1* | 2/2013 | Kirst | G01B 21/085 |
| | | | 73/204.11 |

* cited by examiner

MEASUREMENT DEVICE FOR MEASURING A PROPERTY OF A FLOWING FLUID

TECHNICAL FIELD

The present invention relates to a measurement device, in particular a flow meter, in particular an electromagnetic flow meter, for measuring a property, in particular a flow, of a flowing fluid, comprising a measurement tube having an outer tube and a liner lining the inside of the outer tube, and measurement means for measuring a property of a fluid flowing through the lined measurement tube during measurement operation.

BACKGROUND DISCUSSION

Measurement devices for measuring a property of a fluid flowing through a pipe are commonly used in various branches of industry, for example in the mining or mineral processing industry or in the chemical industry. The measurement data obtained by these devices is e.g. used to control complex industrial processes.

Such measurement devices include e.g. flow meters using different measurement principles, e.g. differential pressure flow meters, electromagnetic flow meters, ultrasonic flow meters, coriolis or vortex flow meters.

In order to be able to measure a property of a flowing fluid, the measurement devices comprise at least one measurement tube, to be inserted in and connected to a pipe, such that at least part of the fluid flowing through the pipe flows through the measurement tube during measurement. Measurement tubes normally consist of metal, e.g. stainless steel and are quite often equipped with a liner, covering the inside of the measurement tube.

Electromagnetic flow meters make use of Faraday's law of induction which states that a voltage is induced in a conductor moving in a magnetic field. In electromagnetic flow meters the fluid flowing through the measurement tube corresponds to the moving conductor. The induced voltage is proportional to the flow velocity and is detected by measuring electrodes. Here a volume flow flowing through the measurement tube is determined based on the measured induced voltage and the inner diameter of the measurement tube. The constant magnetic field is e.g. generated by a switched direct current of alternating polarity. Liners of electromagnetic flow meters consist of electrically insulating materials providing electrical insulation between the measuring electrodes and the measurement tube.

Liners of measurement tubes are directly exposed to the fluid. Depending on the application and/or the properties of the fluid deposits of the fluid may build up on the inside of the liner. In addition the liner may by subject to abrasion, e.g. due to mechanical and/or chemical properties of the fluid, reducing the thickness of the liner.

Deposits as well as abrasion will alter the measurement properties of the device. Thus there is a need in industry to detect either of them at a very early stage, in order to enable the operator to take appropriate countermeasures, long before the device fails or measurement errors exceed a maximum permissible level.

With respect to electromagnetic flow meters abrasion is more critical than accretion, because a decreasing thickness of the liner will directly affect the required insulation between the measurement electrodes and the measurement tube.

U.S. published application, 2013/0031973 A1 describes a method of detecting accretion and/or abrasion of a measurement tube of a Coriolis flow meter, which is in direct contact to the fluid flowing through it. To this extend the flow meter is equipped with two temperature sensors. The first temperature sensor is mounted on an outside wall of the measurement tube, subjected to accretion and/or abrasion. The second temperature sensor is preferably mounted on an outside wall of a pipe segment connected to the measurement tube, in a region, where accretion and/or abrasion is unlikely to occur. Both temperature sensors are applied to measure the temperature prevailing at their location as a function of time. Accretion and/or abrasion is then detected based on a time dependency of the relation of the two temperatures measured as function of time.

In addition Published International Application, WO 2009/134268 A1 describes a method of detecting accretion of a measurement tube of a Coriolis flow meter, which is in direct contact to the fluid flowing through it. Here accretion is detected based on a temperature gradient between spaced apart locations along the flow meter. To this extend temperature sensors are mounted on spaced apart locations on the outside of parts of the flow meter which are exposed to the fluid on their inside, e.g. on an outside wall of a tube inlet and a tube outlet connected to the measurement tube, or on the outside walls of two separate measurement tubes.

Whereas measurement tubes described in the prior art generally consist of metals having a very high thermal conductivity, thermal conductivity of liners, in particular of electrically insulating liners used in electromagnetic flow meters, may be fairly low. Thus even if it may be possible to apply the methods described in US 2013/0031973 A1 or in WO 2009/134268 A1 to measurement devices comprising measurement tubes, which are equipped with liners, the liner will have a noticeable effect on the measured temperatures and the time dependencies of the measured temperatures, which will have to be taken into account.

SUMMARY OF THE INVENTION

It is an object of the invention to provide a measurement device and a method, capable of detecting abrasion of a liner, lining an inside wall of a measurement tube.

To this extent, the invention comprises a measurement device, in particular a flow meter, in particular an electromagnetic flow meter, for measuring a property, in particular a flow, of a flowing fluid, comprising
  a measurement tube comprising an outer tube and a liner lining an inside of the outer tube, and
  measurement means for measuring a property of a fluid flowing through the lined measurement tube during measurement operation,
wherein according to the invention,
  the liner consists of a thermally insulating material, in particular a rubber or a plastic material,
  means are foreseen for measuring a temperature gradient across a measurement tube wall of the measurement tube, when the measurement tube wall is exposed to a temperature difference between an ambient temperature and a fluid temperature of the fluid, and
  detecting means for detecting abrasion of the liner are foreseen, detecting abrasion in case a deviation between the measured temperature gradient and a predetermined reference temperature gradient representing a temperature gradient across a measurement tube wall exposed to the same or at least a similar temperature difference of an identical measurement tube comprising an unimpaired liner exceeds a predetermined limit.

According to a first refinement of the invention, the detecting means comprise calculating means designed to determine a degree of deviation between the measured temperature gradient and the reference temperature gradient and to determine a degree of abrasion of the liner based on the degree of deviation between the measured temperature gradient and the corresponding reference temperature gradient.

According to a second refinement of the invention,
a memory is foreseen, comprising reference data representing a functional dependency of a temperature gradient across the measurement tube wall on the liner thickness for at least one, in particular for several, in particular for a range of temperature differences the measurement tube may be exposed to during operation, and
computing means are foreseen, designed to determine an estimate of a remaining liner thickness of the liner based on the measured temperature gradient, the temperature difference the measurement tube wall was exposed to during measurement of the temperature gradient and the reference data.

According to a third refinement, the measuring means comprise a first temperature sensor for measuring a first temperature prevailing on an inner surface of the liner and a second temperature sensor for measuring a second temperature prevailing on an outside surface of the outer tube.

According to a preferred embodiment of the third refinement
the first temperature sensor is mounted on a tip of an insert, inserted into the measurement tube wall,
the first temperature sensor protrudes into the interior of the measurement tube, and
the second temperature sensor is mounted on an outside surface of the outer tube.

According to a fourth refinement, the first temperature sensor is located in the vicinity of the second temperature sensor with respect to the direction of flow through the measurement tube.

According to a further preferred embodiment the first temperature sensor is exposed to the fluid flowing through the measurement tube during measurement operation.

According to a further preferred embodiment the detecting means are designed to determine said temperature difference between the ambient temperature and the fluid temperature to be equal to a difference between the ambient temperature and the first temperature measured by the first temperature sensor.

According to a further preferred embodiment,
a temperature sensor for measuring an ambient temperature, in particular an external sensor connected to the detecting means or an internal sensor integrated in the detecting means, is foreseen, and
the detecting means are designed to determine the temperature difference between the ambient temperature and the fluid temperature to be equal to a difference between a temperature measured by the temperature sensor for measuring the ambient temperature and the first temperature measured by the first temperature sensor.

According to a fifth refinement of the invention, indicating means, in particular a display, LED's or a signal generator generating an output signal, for indicating abrasion related information, in particular information on whether abrasion of the liner was detected, a degree abrasion detected by the detecting means and/or a remaining thickness of the liner, determined by the detecting means are foreseen.

The invention further comprises a method of detecting abrasion of a liner consisting of a thermally insulating material, in particular a rubber or a plastic material, and lining an inside of an outer tube of a measurement tube of a measurement device, in particular a flow meter, in particular an electromagnetic flow meter, for measuring a property, in particular a flow, of a fluid flowing through the lined measurement tube during measurement operation, wherein according to the invention,
a measurement tube wall of the measurement tube is exposed to a temperature difference between an ambient temperature and a fluid temperature of the fluid flowing through the measurement tube,
a temperature gradient across said measurement tube wall is measured,
a deviation between the measured temperature gradient and a predetermined reference temperature gradient representing a temperature gradient across a measurement tube wall exposed to the same or at least a similar temperature difference of an identical measurement tube comprising an unimpaired liner is determined, and
abrasion of the liner is detected in case the determined deviation exceeds a predetermined limit.

According to a first refinement of the method according to the invention
a degree of deviation between the measured temperature gradient and the reference temperature gradient is determined, and
a degree of abrasion of the liner is determined based on the determined degree of deviation between the measured temperature gradient and the corresponding reference temperature gradient.

According to a second refinement of the method according to the invention
reference data representing a functional dependency of the temperature gradient across the measurement tube wall on the liner thickness is determined for at least one, in particular for several, in particular for a range of temperature differences the measurement tube wall may be exposed to during operation, and
during abrasion detection an estimate of a remaining liner thickness of the liner is determined based on the measured temperature gradient, the temperature difference the measurement tube wall was exposed to during measurement of the temperature gradient and the reference data.

According to a third refinement of the method according to the invention the temperature gradient is determined as a difference between a first temperature measured on an inside of the liner, in particular a first temperature equal to a fluid temperature of the fluid flowing through the measurement tube, and a second temperature measured on an outside surface of the outer tube.

According to a fourth refinement of the method according to the invention the measurements of the first and the second temperature are performed in the vicinity of each other with respect to the direction of flow through the measurement tube.

It is an advantage of the invention that the onset of abrasion of the liner can be detected at a very early stage. This enables the operator of the measurement device or the user of the method according to the invention to take appropriate countermeasures long before the device fails or measurement errors exceed a maximum permissible level.

In addition, based on the degree of abrasion determined and/or the remaining liner thickness determined according to the invention, it is possible to determine a remaining time, for which the device can still be operated safely. In consequence replacements and or repair of liners can be scheduled much more efficiently and economically.

The invention and further advantages are explained in more detail using the figures of the drawing, in which one exemplary embodiment is shown.

DETAILED DESCRIPTION OF THE DRAWINGS

Measurement devices for measuring a property of a flowing fluid according to the invention comprise a measurement tube 1 comprising an outer tube 3 and a liner 5 lining an inside of the outer tube 1 and measurement means for measuring a property of a fluid flowing through the lined measurement tube 1 during measurement operation. The diameter of the measurement tube 1 is preferably set according to an industrial norm and can range from the order of centimeters to decimeters or even up to a meter or more. The outer tube 3 is preferably made out of metal, e.g. out of stainless steel. Depending on the diameter of the measurement tube 1, the outer tube 3 can e.g. have a thickness of several millimeters. The liner 5 is made out of a thermally insulating material, e.g. a rubber, preferably a natural rubber, or a plastic material. To this extent natural rubbers available under the trade name LINATEX® or natural rubbers by Wagu Gummitechnik GmbH can be used. When first put into operation, the liner 5 has an initial liner thickness, e.g. an initial liner thickness in the range of 3 mm to 25 mm.

Figure 1:
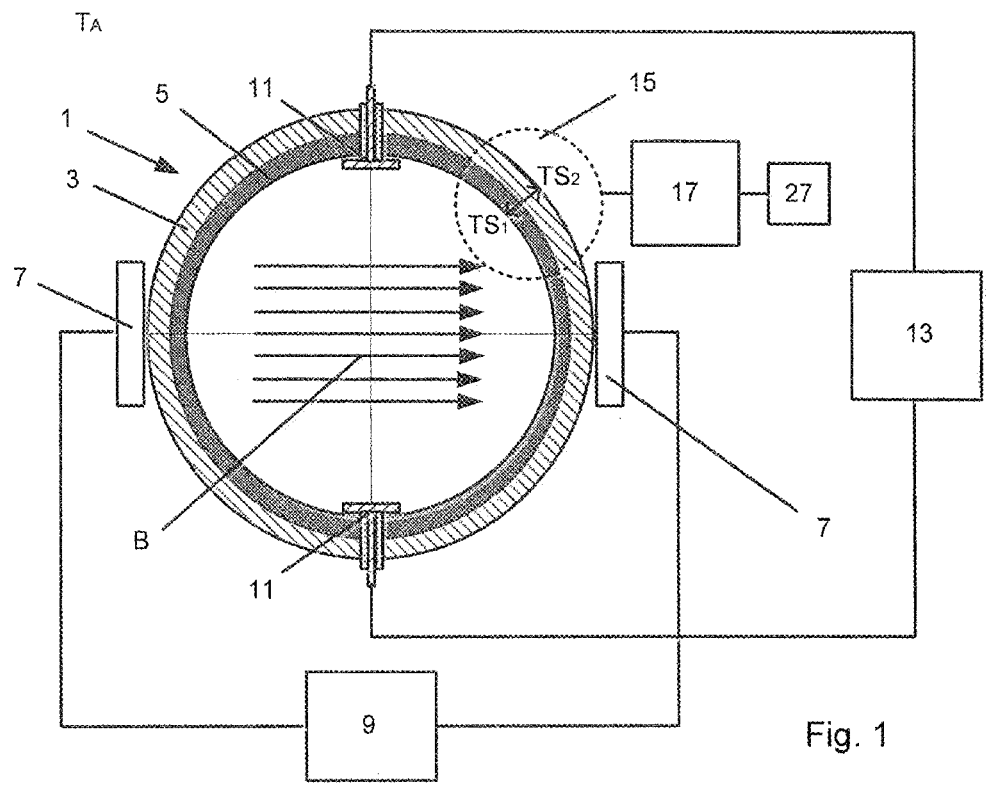
FIG. 1 shows: a schematic diagram of a measurement device.

The measurement device can for example be a flow meter for measuring a flow of a fluid flowing through the lined measurement tube 1. FIG. 1 shows a schematic diagram of a cross section of the measurement tube 1 in a section plane perpendicular to the direction of flow and an exemplary embodiment of measurement means for measuring a property of a fluid flowing through the measurement tube 1 during measurement operation. In the embodiment shown, the measurement device is an electromagnetic flow meter measuring flow based on Faraday's law of induction. In this case, the measurement means comprise means for generating a constant magnetic field B, indicated by arrows in FIG. 1, extending across the lined measurement tube 1 in a direction perpendicular to a longitudinal axis of the measurement tube 1. These means can e.g. comprise a pair of coils 7 mounted diametrically opposite each other on opposite sides on the outside of the measurement tube 1 and a current generator 9 for generating a switched direct current of alternating polarity to be send through the coils 7 in order to generate the magnetic field B.

In addition, the measurement means comprise two measuring electrodes 11 positioned diametrically opposite each other in a direction perpendicular to the magnetic field B on opposing sides on the inside of the measurement tube 1. The electrodes 11 are connected to measurement electronics 13 designed to determine the flow through the measurement tube 1 based on a voltage induced in a direction perpendicular to the magnetic field B and perpendicular to the longitudinal axis of the measurement tube 1.

According to the invention, the measurement device comprises measuring means 15 for measuring a temperature gradient $\Delta T$ across a measurement tube wall of the lined measurement tube 1 schematically shown in FIG. 1. The measuring means 15 are connected to detecting means 17 for detecting abrasion of the liner 5 based on the temperature gradient $\Delta T$.

Figure 2:
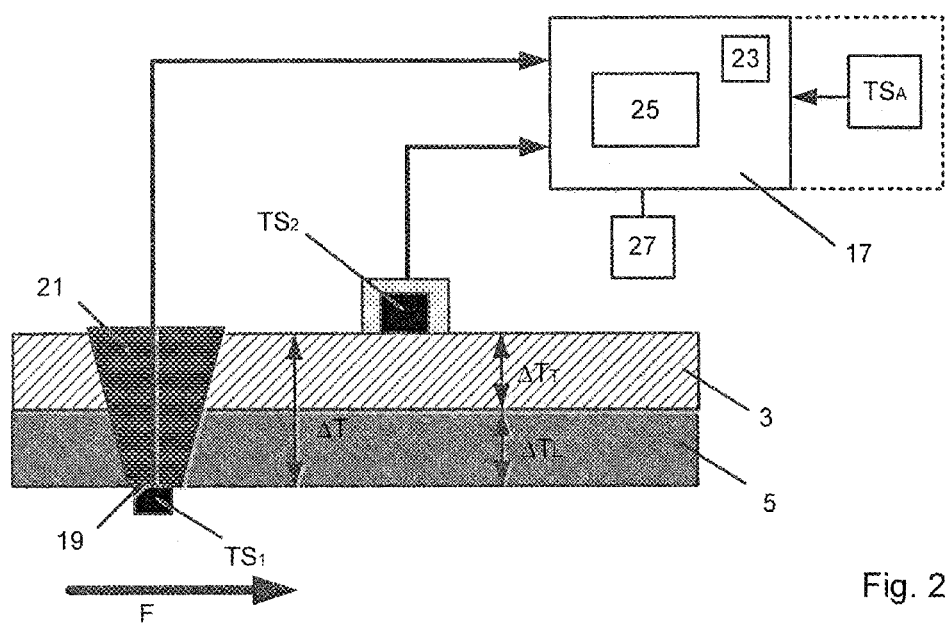
FIG. 2 shows: a longitudinal section of a measurement tube wall of the measurement tube of FIG. 1.

According to a preferred embodiment, the measuring means 15 comprise a first temperature sensor $TS_1$ for measuring a first temperature $T_1$ prevailing on an inner surface of the liner 5 and a second temperature sensor $TS_2$ for measuring a second temperature $T_2$ prevailing on an outside surface of the outer tube 3. FIG. 2 shows a longitudinal cross section of a section of the measurement tube wall of the measurement tube 1 of FIG. 1 equipped with the two temperature sensors $TS_1$, $TS_2$. The first temperature sensor $TS_1$ can e.g. be mounted on a tip 19 of an insert 21, inserted into the measurement tube wall, such that the temperature sensors $TS_1$ protrudes into the interior of the measurement tube 1. During measurement, the first temperature sensor $TS_1$ is exposed to the fluid flowing through the measurement tube 1. In consequence, the first temperature $T_1$ corresponds to the fluid temperature $T_L$. The insert 21 can e.g. be designed in the same way as inserts for mounting electrodes exposed to the fluid during measurement. Corresponding mounting means are known in the art, and thus not described in detail herein.

The first temperature sensor $TS_1$ can be mounted individually. Alternatively, it can be included in a tip of an insert comprising a monitoring electrode for monitoring a filling level inside the measurement tube 1. An monitoring electrode comprising an integrated temperature sensor for measuring the fluid temperature is e.g. described in German Application, DE 10 2012 109 308 A1.

The two temperature sensors $TS_1$, $TS_2$ are preferably located in the vicinity of each other with respect to the direction of flow F, indicated by arrow F in FIG. 2. In applications, where the fluid temperature $T_L$ can be expected to be fairly constant throughout the length of the measurement tube 1, the two temperature sensors $TS_1$, $TS_2$ can be located in spaced apart locations along the measurement tube 1.

Provided that there is a temperature difference $\Delta T_{L/A}$ between an ambient temperature $T_A$ prevailing in the surrounding of the measurement device and the fluid temperature $T_L$, heat is transferred by conduction through the lined measurement tube 1. Considering, that the ambient temperature for most applications typically ranges from 0° C. up to 35° C. and fluid temperatures can range to temperatures of up to 160° C., there is a wide variety of applications where fairly large temperature differences $\Delta T_{L/A}$ occur. The heat transferred depends on the temperature difference $\Delta T_{L/A}$ between the ambient temperature $T_A$ and the fluid temperature $T_L$ causing it. In addition the heat transfer depends on the thermal conductivity, the shape and the dimensions of the outer tube 3 and the thermal conductivity, the shape and the dimensions of the liner 5.

The temperature gradient $\Delta T$ across the wall segment can e.g. be calculated to be equal to a difference between the first and the second temperature $\Delta T = T_1 - T_2$. As indicated in FIG. 2, the temperature gradient $\Delta T$ across the wall of the measurement tube 1 corresponds to a sum of a temperature gradient $\Delta T_L$ across the liner 5 and a temperature gradient $\Delta T_T$ across the outer tube 3. Since the outer tube 3 normally consists of metal and metals are excellent heat conductors, the temperature gradient $\Delta T_T$ across the outer tube 3 will in most case be very small or even negligible. In contrast to this, a temperature gradient $\Delta T_L$ of measurable size will establish across the liner 5 due to its thermally insulating material properties. As an example, stainless steel has a thermal conductivity of more than 10 W/(m K), e.g. 16 W/(m K)-19 W/(m K), whereas natural rubber has a thermal conductivity of the order of 0.1 W/(m K), e.g. of 0.13 W/(m K).

During operation of the measurement device the thermal conductivity, the shape and the dimensions of the outer tube 3 and the thermal conductivity and the shape of the liner 5 remain constant. In consequence, the temperature gradient $\Delta T$ measured by the temperature sensors $TS_1$, $TS_2$ can be described by a function of a set of at least one constant parameter and two variables, namely the temperature difference $\Delta T_{L/A}$ between the fluid temperature $T_L$ and the ambient temperature $T_A$ and the dimensions of the liner 5. Since the shape and the outer diameter of the liner 5 are kept constant by the outer tube 3 connected to it, changes in the dimensions of the liner 5 can be considered to be solely due to changes in liner thickness caused by abrasion.

In many applications, the ambient temperature $T_A$ is a known fairly constant temperature, e.g. room temperature. In this case the ambient temperature $T_A$ can be stored in a memory 23 integrated in or accessible to the detecting means 17. In applications, where this is not the case or in order to improve the accuracy of the detection method according to the invention, a temperature senor $TS_A$ for measuring the ambient temperature $T_A$ can be foreseen. This sensor can e.g. be an external sensor connected to the detecting means 17 or an internal sensor, which can e.g. be integrated in the detecting means 17 as indicated by the dotted line in FIG. 2. In both cases, the temperature difference $\Delta T_{L/A}$ between the ambient temperature $T_A$ and the fluid temperature $T_L$ can be calculated by the detecting means 17 to equal: $\Delta T_{L/A} = T_A - T_L$, wherein $T_A$ corresponds to the measured or stored ambient temperature and $T_L$ corresponds to the fluid temperature measured by the first temperature sensor $TS_1$.

The detecting means 17 comprise computing means 25 for determining a deviation between the measured temperature gradient $\Delta T$ across the measurement tube wall exposed to the measured temperature difference $\Delta T_{L/A}$ and a predetermined reference temperature gradient $\Delta T_{ref}(\Delta T_{L/A})$ representing the temperature gradient across the measurement tube wall exposed to the same or at least a similar temperature difference $\Delta T_{L/A}$ of an identical measurement tube 1 comprising an unimpaired liner 5. The reference temperature gradients $\Delta T_{ref}(\Delta T_{L/A})$ can either be determined experimentally or numerically and are preferably stored together with the corresponding temperature difference $\Delta T_{L/A}$ in memory 23.

The deviation can e.g. be determined as a ratio of the measured temperature gradient $\Delta T$ and the corresponding reference temperature gradient $\Delta T_{ref}(\Delta T_{L/A})$ or as a difference between the measured temperature gradient $\Delta T$ and the corresponding reference temperature gradient $\Delta T_{ref}(\Delta T_{L/A})$.

The detecting means 17 are set up to detect the presence of abrasion of the liner 5 in case the deviation exceeds a predetermined limit, e.g. in case the determined difference exceeds a predetermined threshold or the determined ratio falls below a predetermined threshold.

Increasing abrasion of the liner 5 will increase the degree of deviation between the measured temperature gradient $\Delta T$ and the corresponding reference temperature gradient $\Delta T_{ref}(\Delta T_{L/A})$. The detecting means 17 are therefore preferably set up to determine a degree of abrasion of the liner 5 present based on the degree of deviation between the measured temperature gradient $\Delta T$ and the corresponding reference temperature gradient $\Delta T_{ref}(\Delta T_{L/A})$.

As already described above, the temperature gradient $\Delta T$ across a measurement tube wall exposed to a certain temperature difference $\Delta T_{L/A}$ depends on the liner thickness. This can be used to refine the detection capabilities of the detecting means 17. To this extend, the functional dependency of the temperature gradient $\Delta T$ on the liner thickness is preferably determined either experimentally for at least one, preferably for several or even for a range of temperature differences $\Delta T_{L/A}$ and stored as reference data in memory 23 associated to the detecting means 17.

In this case, the computing means 25 are preferably designed to calculate an estimate for a remaining thickness of the liner 5 based on the measured temperature gradient $\Delta T$, the measured temperature difference $\Delta T_{L/A}$ and the corresponding reference data representing the dependency of the temperature gradient across the measurement tube wall exposed to the respective temperature difference $\Delta T_{L/A}$ as a function the thickness of the liner 5.

The measurement device preferable comprises indicating means 27, e.g. a display, LED's or a signal generator generating an output signal, for indicating abrasion related information determined by the detecting means 17. This information preferable comprises information on whether abrasion of the liner 5 was detected, the degree abrasion in case abrasion was detected and/or the remaining thickness of the liner 5 determined by the detecting means 17.

Even though the invention was described above, with respect to an electromagnetic flow meter, it can be applied in the same way to other measurement devices comprising measurement tubes, comprising an outer tube and an inner liner, wherein a fluid flows through the measurement tube during operation and wherein the liner consists of a thermally insulating material.

What is claimed is:

1. A measurement device, for measuring flow, of a flowing fluid, comprising:
   a measurement tube, having an outer tube and a liner lining an inside of said outer tube;
   wherein said liner consists of a thermally insulating material; and
   wherein a measuring tube wall of said measurement tube is exposed to a temperature difference ($\Delta T_{L/A}$) between an ambient temperature ($T_A$) and a fluid temperature ($T_L$) of the fluid flowing through said measurement tube during measurement operation;
   measurement means for measuring the fluid flowing through said lined measurement tube during a measurement operation;
   means for measuring a temperature gradient ($\Delta T$) across said measurement tube wall, wherein said temperature gradient ($\Delta T$) is given by a temperature difference between a first temperature ($T_1$) prevailing on an inner surface of said liner and a second temperature ($T_2$) prevailing on an outside surface of said outer tube, and wherein said means for measuring said temperature gradient ($\Delta T$) comprise a first temperature sensor ($TS_1$) measuring said first temperature ($T_1$) and a second temperature sensor ($TS_2$) measuring said second temperature ($T_2$);
   detecting means for detecting abrasion of said liner, wherein said detecting means determine a deviation between said measured temperature gradient ($\Delta T$) and a predetermined stored reference temperature gradient ($\Delta T_{ref}(\Delta T_{L/A})$) representing a temperature gradient across a measurement tube wall exposed to the same or at least a similar temperature difference ($\Delta T_{L/A}$) of an identical measurement tube comprising an unimpaired liner and detect abrasion when the deviation exceeds a predetermined limit.

2. The measurement device according to claim 1, wherein:
said detecting means comprise calculating means designed to determine a degree of deviation between said measured temperature gradient ($\Delta T$) and said reference temperature gradient ($\Delta T_{ref}(\Delta T_{L/A})$) and to determine a degree of abrasion of said liner based on the degree of deviation between the measured temperature gradient ($\Delta T$) and the corresponding reference temperature gradient ($\Delta T_{ref}(\Delta T_{L/A})$).

3. The measurement device according to claim 1, further comprising:
a memory, comprising reference data representing a functional dependency of a temperature gradient across said measurement tube wall on the liner thickness determined for at least one, for several, or for a range of temperature differences ($\Delta T_{L/A}$); and
computing means, designed to determine an estimate of a remaining liner thickness of said liner based on the measured temperature gradient ($\Delta T$), the temperature difference ($\Delta T_{L/A}$) the measurement tube wall was exposed to during measurement of the temperature gradient ($\Delta T$) and said reference data.

4. The measurement device according to claim 1, wherein:
said first temperature sensor ($TS_1$) is mounted on a tip of an insert, inserted into said measurement tube wall;
said first temperature sensor ($TS_1$) protrudes into the interior of said measurement tube; and
said second temperature sensor ($T_2$) is mounted on an outside surface of said outer tube.

5. The measurement device according to claim 1, wherein:
said first temperature sensor ($TS_1$) is located in the vicinity of said second temperature sensor ($TS_2$) with respect to the direction of flow through said measurement tube.

6. The measurement device according to claim 1, wherein:
said first temperature sensor ($TS_1$) is exposed to said fluid flowing through said measurement tube during measurement operation.

7. The measurement device according to claim 1, wherein:
said detecting means are designed to determine said temperature difference ($\Delta T_{L/A}$) between said ambient temperature ($T_A$) and said fluid temperature ($T_L$) to be equal to a difference between said ambient temperature ($T_A$) and said first temperature ($T_1$) measured by said first temperature sensor ($TS_1$).

8. The measurement device according to claim 1, further comprising:
a temperature sensor ($TS_A$) for measuring an ambient temperature ($T_A$), namely an external sensor connected to said detecting means or an internal sensor integrated in said detecting means, wherein:
said detecting means are designed to determine said temperature difference ($\Delta T_{L/A}$) between said ambient temperature ($T_A$) and said fluid temperature ($T_L$) to be equal to a difference between a temperature measured by said temperature sensor ($TS_A$) for measuring said ambient temperature ($T_A$) and said first temperature ($T_1$) measured by said first temperature sensor ($TS_1$).

9. The measurement device according to claim 1, further comprising:
indicating means, for indicating abrasion related information, on an abrasion of said liner detected by said detecting means, a degree abrasion detected by said detecting means and/or a remaining thickness of said liner, determined by said detecting means are foreseen.

10. The measuring device according to claim 1, wherein said outer tube consists of a heat conducting metal and said liner consists of a thermally insulating rubber or plastic.

11. A method of detecting abrasion of a liner consisting of a thermally insulating material, and lining an inside of an outer tube of a measurement tube of a flow meter, measuring a flow of a fluid flowing through the lined measurement tube during a measurement operation, the method comprising the steps of:
exposing a measurement tube wall of the measurement tube to a temperature difference ($\Delta T_{L/A}$) between an ambient temperature ($T_A$) and a fluid temperature ($T_L$) of the fluid flowing through said measurement tube;
measuring a temperature gradient ($\Delta T$) across said measurement tube wall;
wherein said temperature gradient ($\Delta T$) is determined as a temperature difference between a first temperature ($T_1$) prevailing on an inner surface of said liner and a second temperature ($T_2$) prevailing on an outside surface of said outer tube; and
wherein said first temperature ($T_1$) is measured on an inside of said liner and said second temperature ($T_2$) is measure on an outside surface of said outer tube;
determining a deviation between the measured temperature gradient ($\Delta T$) and a predetermined stored reference temperature gradient ($\Delta T_{ref}(\Delta T_{L/A})$) representing a temperature gradient across a measurement tube wall exposed to the same or at least a similar temperature difference ($\Delta T_{L/A}$) of an identical measurement tube comprising an unimpaired liner; and
detecting abrasion of the liner when the determined deviation exceeds a predetermined limit.

12. The method according to claim 11, comprising the steps of:
determining a degree of deviation between the measured temperature gradient ($\Delta T$) and said reference temperature gradient ($\Delta T_{ref}(\Delta T_{L/A})$); and
determining a degree of abrasion of the liner based on said determined degree of deviation between the measured temperature gradient ($\Delta T$) and the corresponding reference temperature gradient ($\Delta T_{ref}(\Delta T_{L/A})$).

13. The method according to claim 11, further comprising the steps of:
determining reference data representing a functional dependency of the temperature gradient ($\Delta T$) across the measurement tube wall on the liner thickness for at least one, for several, or for a range of temperature differences ($\Delta T_{L/A}$); and
determining during abrasion detection, an estimate of a remaining liner thickness of the liner based on the measured temperature gradient ($\Delta T$), the temperature difference ($\Delta T_{L/A}$) the measurement tube wall was exposed to during measurement of the temperature gradient ($\Delta T$) and the reference data.

14. The method according to claim 11, wherein:
the measurements of the first and the second temperature ($T_1$, $T_2$) are performed in the vicinity of each other with respect to the direction of flow through the measurement tube.

15. A measurement device for measuring flow, of a flowing fluid, comprising:
- a measurement tube, having an outer tube and a liner lining an inside of said outer tube; wherein said liner consists of a thermally insulating material; and
- wherein a measurement tube wall of said measurement tube is exposed to a temperature difference ($\Delta T_{L/A}$) between an ambient temperature ($T_A$) and a fluid temperature ($T_L$) of the fluid flowing through said measurement tube during measurement operation;
- measurement means measuring the flow of the fluid flowing through said lined measurement tube during measurement operation;
- means for measuring a temperature gradient ($\Delta T$) across said measurement tube wall, wherein said temperature gradient ($\Delta T$) is given by a temperature difference between a first temperature ($T_1$) prevailing on an inner surface of said liner and a second temperature ($T_2$) prevailing on an outside surface of said outer tube, and wherein said means for measuring said temperature gradient ($\Delta T$) comprise a first temperature sensor ($TS_1$) measuring said first temperature ($T_1$) and a second temperature sensor ($TS_2$) measuring said second temperature ($T_2$); and
- detecting means for detecting abrasion of said liner, wherein said detecting means determine a deviation between said measured stored temperature gradient ($\Delta T$) and a predetermined reference temperature gradient ($\Delta T_{ref}(\Delta T_{L/A})$) representing a temperature gradient across a measurement tube wall exposed to the same or at least a similar temperature difference ($\Delta T_{L/A}$) of an identical measurement tube comprising an unimpaired liner and detect abrasion when the deviation exceeds a predetermined limit;
- a memory, comprising reference data representing a functional dependency of a temperature gradient across said measurement tube wall on the liner thickness determined for at least one, for at least one, for several or for a range of temperature differences ($\Delta T_{L/A}$); and
- computing means, designed to determine an estimate of a remaining liner thickness of said liner based on the measured temperature gradient ($\Delta T$), the temperature difference ($\Delta T_{L/A}$) the measurement tube wall was exposed to during measurement of the temperature gradient ($\Delta T$) and said reference data.

* * * * *